US012714358B2

(12) United States Patent
Donevant et al.

(10) Patent No.: US 12,714,358 B2
(45) Date of Patent: Aug. 25, 2026

(54) METHOD FOR USING INFRARED TECHNOLOGY TO DETECT TISSUE DAMAGE BELOW THE SKIN

(71) Applicant: UNIVERSITY OF SOUTH CAROLINA, Columbia, SC (US)

(72) Inventors: Sara Donevant, Bethune, SC (US); Robin Dawson, Lancaster, SC (US); Brandon Percival, Lancaster, SC (US); William Harris, IV, Rock Hill, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 18/624,203

(22) Filed: Apr. 2, 2024

(65) Prior Publication Data

US 2024/0324948 A1 Oct. 3, 2024

Related U.S. Application Data

(60) Provisional application No. 63/493,876, filed on Apr. 3, 2023.

(51) Int. Cl.
*A61B 5/00* (2006.01)
*A61B 5/01* (2006.01)
(Continued)

(52) U.S. Cl.
CPC ............ *A61B 5/447* (2013.01); *A61B 5/0075* (2013.01); *A61B 5/015* (2013.01); *A61B 5/6898* (2013.01);
(Continued)

(58) Field of Classification Search
CPC . G06T 2207/10048; G06T 2207/20081; G06T 2207/20084; G06T 2207/20212;
(Continued)

(56) References Cited

U.S. PATENT DOCUMENTS

| | | | | |
|---|---|---|---|---|
| 11,538,157 | B1 * | 12/2022 | Schoess | A61B 5/024 |
| 2017/0127999 | A1 * | 5/2017 | Linders | G16H 50/20 |
| 2019/0385308 | A1 * | 12/2019 | Kandlikar | A61B 5/4312 |

FOREIGN PATENT DOCUMENTS

| | | | | |
|---|---|---|---|---|
| CN | 114888870 A * | 8/2022 | | A61B 5/0013 |
| WO | WO-2022159093 A1 * | 7/2022 | | A61B 5/0013 |

OTHER PUBLICATIONS

I. Cruz-Vega et al., "Deep Learning Classification for Diabetic Foot Thermograms," 2020, Sensors, 20(6), 1762 (Year: 2020).*

* cited by examiner

*Primary Examiner* — Michael J Carey
*Assistant Examiner* — Maria Christina Talty
(74) *Attorney, Agent, or Firm* — Dority & Manning, P.A.

(57) ABSTRACT

The disclosure deals with methodology and involved or associated systems for using infrared technology to detect tissue damage below the skin. Pressure and shear stress can damage the microvascular structure below the skin, which is not visible to the naked eye. Infrared thermography is a non-invasive mechanism to measure skin temperature via thermal radiation. Changes (restrictions) in blood flow below the skin can result in microvascular damage to the tissue, and directly impact skin temperature, which can be detected by infrared thermography. Infrared thermography can detect these changes at the site of tissue damage. This disclosure uses affordable infrared thermography to detect changes in temperature related to blood flow alterations, supported with AI. Using serial images, AI can detect an emerging DFU (Diabetic Foot Ulcer) in DM (Diabetes Mellitus) patients through deviations in skin temperature.

17 Claims, 4 Drawing Sheets

(51) Int. Cl.
*G06T 7/00* (2017.01)
*G06T 7/194* (2017.01)
*G16H 10/60* (2018.01)
*G16H 50/20* (2018.01)

(52) U.S. Cl.
CPC .......... *A61B 5/7267* (2013.01); *A61B 5/7282* (2013.01); *G06T 7/0016* (2013.01); *G06T 7/194* (2017.01); *G16H 10/60* (2018.01); *G16H 50/20* (2018.01); *G06T 2207/10048* (2013.01); *G06T 2207/20081* (2013.01); *G06T 2207/20084* (2013.01); *G06T 2207/20212* (2013.01); *G06T 2207/30088* (2013.01)

(58) Field of Classification Search
CPC ......... G06T 2207/30088; G06T 7/0016; G06T 7/194; A61B 5/0075; A61B 5/0077; A61B 5/015; A61B 5/447; A61B 5/6898; A61B 5/7267; A61B 5/7282; G16H 10/60; G16H 30/40; G16H 50/20
See application file for complete search history.

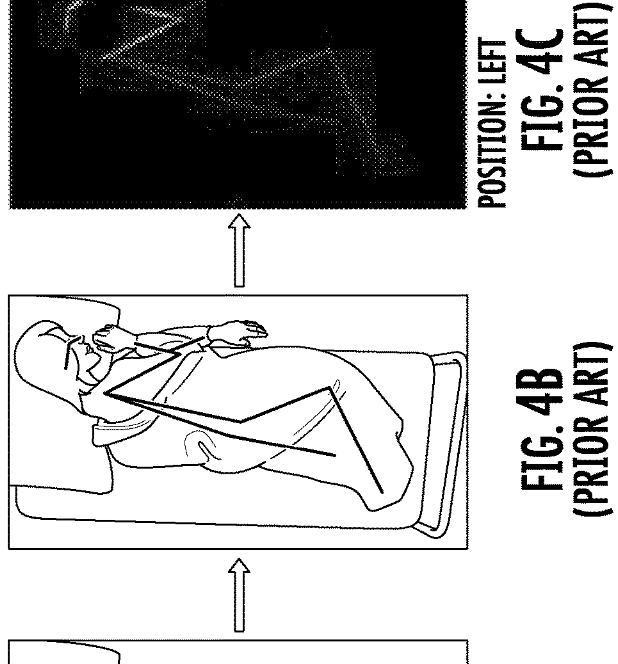
FIG. 4A
FIG. 4B (PRIOR ART)
FIG. 4C (PRIOR ART)
FIG. 5
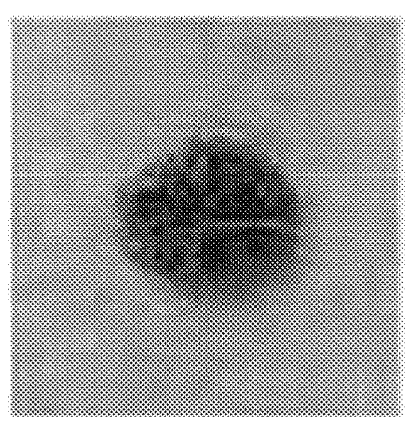
FIG. 6A
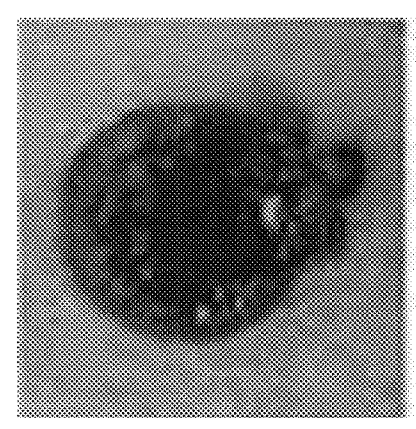
FIG. 6B

METHOD FOR USING INFRARED TECHNOLOGY TO DETECT TISSUE DAMAGE BELOW THE SKIN

PRIORITY CLAIM

The present application claims the benefit of priority of U.S. Provisional Patent Application No. 63/493,876, titled Infrared Technology To Detect Tissue Damage Below The Skin, filed Apr. 3, 2023, and which is fully incorporated herein by reference for all purposes.

BACKGROUND OF THE PRESENTLY DISCLOSED SUBJECT MATTER

Pressure and shear stress can damage the microvascular structure below the skin, which is not visible to the naked eye. Once the pressure and stress are relieved, blood flow returns to the damaged tissue, starting the swing phase.

Every year, 9.1 to 26.1 million patients with diabetes mellitus (DM) develop a diabetic foot ulcer (DFU). Neuropathy and ischemia are vital factors impacting the development of a DFU in conjunction with calluses and drying of the skin. When these conditions are combined with pressure and shear stress, damage to the microvascular structure begins.

Once the pressure and stress are relieved, blood flow returns to the damaged tissue starting the swing phase. This pathway results in cellular necrosis causing a DFU. Globally, half of the DFUs will become infected, and almost a quarter will result in amputation. Patients with DFUs experience an increased risk of co-morbidities and complications, including an increased mortality risk with amputation. Among patients with an amputation, over 50% die within five years.

Diabetic foot ulcers impact 15% of all diabetic patients in U.S. In 2017, approximately $79 billion was spent on care for DFUs, or about $8600 per patient. The costs associated with DFUs continue to increase each year, suggesting alternative approaches to detection and early management are needed.

Current standards of care recommend foot inspections by podiatrists. 8,840 podiatrists in the US monitor patients with diabetes mellitus. However, in rural and underserved areas, patients with DM can experience significant barriers to attending regular podiatry visits, such as access to podiatrists and transportation. Additionally, foot inspection depends on human visualization of erythema, which can be missed. Late identification of DFUs is more common in people of color, who experience a significantly higher rate of amputation and longer hospital stays than white patients with DFUs and neuropathy. 85% of all amputations in diabetic patients (≈73,000 patients) originate from foot ulcers.

DFUs can also develop between the permitted 9-week foot inspection appointments, creating a delay in early identification and treatment.

One attempt at a solution to the overall problem uses heat and/or pressure-sensing insoles worn inside a DM patient's shoes. However, this solution only examines the pressure and heat on the plantar aspect of the foot. Recent studies show that only 38% of DFUs occur at the site of maximum pressure, thus leaving gaps in the screening process. Further, the relative foot temperature with loadbearing activity and synthetic footwear may not necessarily indicate a DFU.

However, existing studies involving infrared thermography and DFUs focus on detecting an increase in the relative temperature of a foot with a DFU and rely on human analysis of the images and data. These systems do not incorporate AI to assist the provider with identifying skin temperature changes. Additionally, typical infrared thermography systems used in the current research range from $15,000 to $50,000, which is cost-prohibitive for many healthcare providers and home health agencies. All these issues serve as significant barriers to identifying DFU early in the development process. Therefore, the presently disclosed subject matter seeks to change the paradigm by using affordable infrared thermography to detect changes in temperature related to blood flow alterations supported with AI.

The presently disclosed system would offer competitive advantages over existing technology, for example, by examining all aspects of a patient's foot, not just the sole of the foot. In other aspects, the presently disclosed technology can be beneficially provided through an implementation using, for example a tablet such as an iPad®, coupled with a thermal imaging camera such as a FLIR One® Pro for smartphones.

SUMMARY OF THE PRESENTLY DISCLOSED SUBJECT MATTER

The disclosure deals with system and methodology for using infrared technology to detect tissue damage below the skin. Infrared thermography is a non-invasive mechanism to measure skin temperature via thermal radiation. Changes (restrictions) in blood flow below the skin can result in microvascular damage to the tissue, and directly impact skin temperature. Infrared thermography can detect these changes at the site of tissue damage. Using serial images, AI can detect an emerging DFU (Diabetic Foot Ulcers) in DM (Diabetes Mellitus) patients through deviations in skin temperature.

The presently disclosed subject matter seeks to change the tissue damage detection paradigm by using affordable infrared thermography to detect changes in temperature related to blood flow alterations supported with AI.

For some embodiments, the presently disclosed subject matter relates to improvements in skin inspection for microvascular injury, using infrared thermography with AI and decision support.

In DM patients, infrared thermography can measure the skin temperature changes associated with the phases at the site of the tissue damage. Decreased skin temperature at the site due to restricted blood flow can result in microvascular damage to the tissue. Increased skin temperature at the site of tissue damage increases during the swing phase due to the return of blood flow and inflammation cascade.

For some embodiments, using thermography to identify changes in skin temperature due to damage below the skin can detect damage that may later result in an open wound. For some aspects of some presently disclosed embodiments, artificial intelligence (AI) can be used to detect changes in skin temperature over time to identify the damage early in the process. Early detection can allow for informed intervention actions to prevent further damage and improve patient outcomes.

In addition to monitoring for tissue damage in diabetic patients, the presently disclosed technology can also be used to detect melanoma, necrotic colitis, or any other condition where a temperature change occurs due to an inflammatory response or other type of response.

In one exemplary embodiment disclosed herewith, methodology is provided for detecting tissue damage below the skin of a patient. Such exemplary methodology preferably comprises capturing a plurality of time-spaced infrared thermography image data for selected regions of skin of a patient; recording the ambient temperatures at the selected regions at each time that the plurality of time-spaced infrared thermography image data is captured; and uploading the captured image data and recorded ambient temperatures into a trained machine-learning model, wherein the machine-learning model is trained to identify deviations in skin temperature of the patient and detect tissue damage below the skin of the patient based on identified skin temperature deviations.

It is to be understood that the presently disclosed subject matter equally relates to devices, systems, and associated and/or corresponding methodologies.

Other example aspects of the present disclosure are directed to systems, apparatus, tangible, non-transitory computer-readable media, user interfaces, memory devices, and electronic devices for detecting tissue damage below the skin. To implement methodology and technology herewith, one or more processors may be provided, programmed to perform the steps and functions as called for by the presently disclosed subject matter, as will be understood by those of ordinary skill in the art.

For some embodiments of the foregoing exemplary methodology, the machine-learning model may be trained to identify to detect changes in temperature related to blood flow alterations, and detect an emerging DFU (Diabetic Foot Ulcer) in a DM (Diabetes Mellitus) patient through identified deviations in skin temperature.

For other exemplary embodiments, capturing a plurality of time-spaced infrared thermography image data may comprise a user using a smartphone equipped with infrared thermography to take pictures of selected regions of skin, at predetermined frequency between image captures. For some of those embodiments, the selected regions of skin comprise high-risk areas. For others, the high-risk areas may more specifically comprise bony areas with minimal fat included but not limited to one of a patient's coccyx, shoulder blades, heels, and elbows.

For some other embodiments of the foregoing exemplary methodology, the machine-learning model may be trained to assess image data to detect changes over time, and provide decision support in real-time to medical personnel regarding patient course of treatment.

For yet others, the machine-learning model comprises a convolution neural network with multiple convolutional layers.

Some embodiments may further comprise processing the captured image data before being uploaded to the trained machine-learning model as processed image data. For some such embodiments, processing the captured data may include removing background in the image created with the infrared thermography image data to eliminate any potential external interference with the analysis, to generate a white image on a black background; integrating a thermal image into the white image; imposing a grid pattern on the integrated thermal and white image and creating cells organized in rows and columns; integrating the grid pattern into thermal data aggregated on the white image and averaging the temperature value in each cell; and uploading the resulting data into the machine-learning model.

For some of the embodiments, processing the captured data may include providing one or more processors; and one or more non-transitory computer-readable media that store instructions that, when executed by the one or more processors, cause the one or more processors to perform operations. Preferably, for some such embodiments, the operations may comprise removing background in the image created with the infrared thermography image data to eliminate any potential external interference with the analysis, to generate a white image on a black background; integrating a thermal image into the white image; imposing a predetermined grid pattern on the integrated thermal and white image; integrating the grid pattern into thermal data aggregated on the white image; and uploading the resulting data into the machine-learning model. For some of the foregoing embodiments, the machine-learning model may be trained to perform a cell-by-cell comparison to generate a second grid-like image that contains the temperature difference in each cell; and perform anomaly detection and condition predictions.

For yet other embodiments of the foregoing exemplary methodology, processing the captured data may include conducting image data processing steps of segmentation, transformation, composition, tabulation, and aggregation, per a grid pattern imposed on the image data.

For some others, providing decision support may further include making automatic entries in Electronic Health Records (EHR) for retrieval by authorized medical personnel regarding patient course of treatment including informed intervention actions.

For yet others, the machine-learning model may be trained to detect and identify at least one of tissue damage in diabetic patients, melanoma, necrotic colitis in pre-term infants, and any other condition where a temperature change occurs due to an inflammatory response or other type of response.

Another exemplary such method relates to methodology for using infrared technology for detecting tissue damage below the skin of a patient. Such exemplary methodology preferably comprises using a smartphone equipped with infrared thermography to capture a plurality of time-spaced infrared thermography image data to take pictures of selected regions of skin of a patient, at predetermined frequency between image captures; recording the ambient temperatures at the selected regions at each time that the plurality of time-spaced infrared thermography image data is captured; processing the captured image data; and uploading the processed image data and recorded ambient temperatures into a trained machine-learning model, wherein the machine-learning model is trained to assess image data to detect changes over time to identify deviations in skin temperature of the patient, to detect tissue damage below the skin of the patient based on identified skin temperature deviations, and to provide decision support in real-time to medical personnel regarding patient course of treatment. For such exemplary embodiment, the machine-learning model is preferably trained to detect and identify at least one of tissue damage in diabetic patients, melanoma, necrotic colitis in pre-term infants, and any other condition where a temperature change occurs due to an inflammatory response or other type of response.

Additional objects and advantages of the presently disclosed subject matter are set forth in, or will be apparent to, those of ordinary skill in the art from the detailed description herein. Also, it should be further appreciated that modifications and variations to the specifically illustrated, referred and discussed features, elements, and steps hereof may be practiced in various embodiments, uses, and practices of the presently disclosed subject matter without departing from the spirit and scope of the subject matter. Variations may include, but are not limited to, substitution of equivalent means, features, or steps for those illustrated, referenced, or discussed, and the functional, operational, or positional reversal of various parts, features, steps, or the like.

Still further, it is to be understood that different embodiments, as well as different presently preferred embodiments, of the presently disclosed subject matter may include various combinations or configurations of presently disclosed features, steps, or elements, or their equivalents (including combinations of features, parts, or steps or configurations thereof not expressly shown in the figures or stated in the detailed description of such figures). Additional embodiments of the presently disclosed subject matter, not necessarily expressed in the summarized section, may include and incorporate various combinations of aspects of features, components, or steps referenced in the summarized objects above, and/or other features, components, or steps as otherwise discussed in this application. Those of ordinary skill in the art will better appreciate the features and aspects of such embodiments, and others, upon review of the remainder of the specification, and will appreciate that the presently disclosed subject matter applies equally to corresponding methodologies as associated with practice of any of the present exemplary devices, and vice versa.

These and other features, aspects and advantages of various embodiments will become better understood with reference to the following description and appended claims. The accompanying drawings, which are incorporated in and constitute a part of this specification, illustrate embodiments of the present disclosure and, together with the description, serve to explain the related principles.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which:

FIGS. 2(*b*) through 2(*e*) respectively illustrate a recognized progression of stages of microvascular damage (specifically, development of pressure ulcers) referred to as Stage 1, Stage 2, Stage 3, and Stage 4, respectively;

FIG. 4(*a*) illustrates a simple image of a patient positioned on a support, as viewed from a position directly above the patient;

FIG. 4(*b*) (Prior Art) represents augmentation of the image of FIG. 4(*a*) by an associated AI-based system, to add lines representing the position of the patient's limbs and torso per the AI-based system analysis;

FIG. 4(*c*) (Prior Art) illustrates the added lines of FIG. 4(*b*) in isolation, coupled with a determination by the AI-based system that the patient is positioned on their left side;

FIG. 5 illustrates an image of an example of a patient suffering with the impact of diabetic foot ulcers;

FIGS. 6(*a*) and 6(*b*) illustrate respective images of examples of detected melanoma of a patient's skin;

Figure 1:
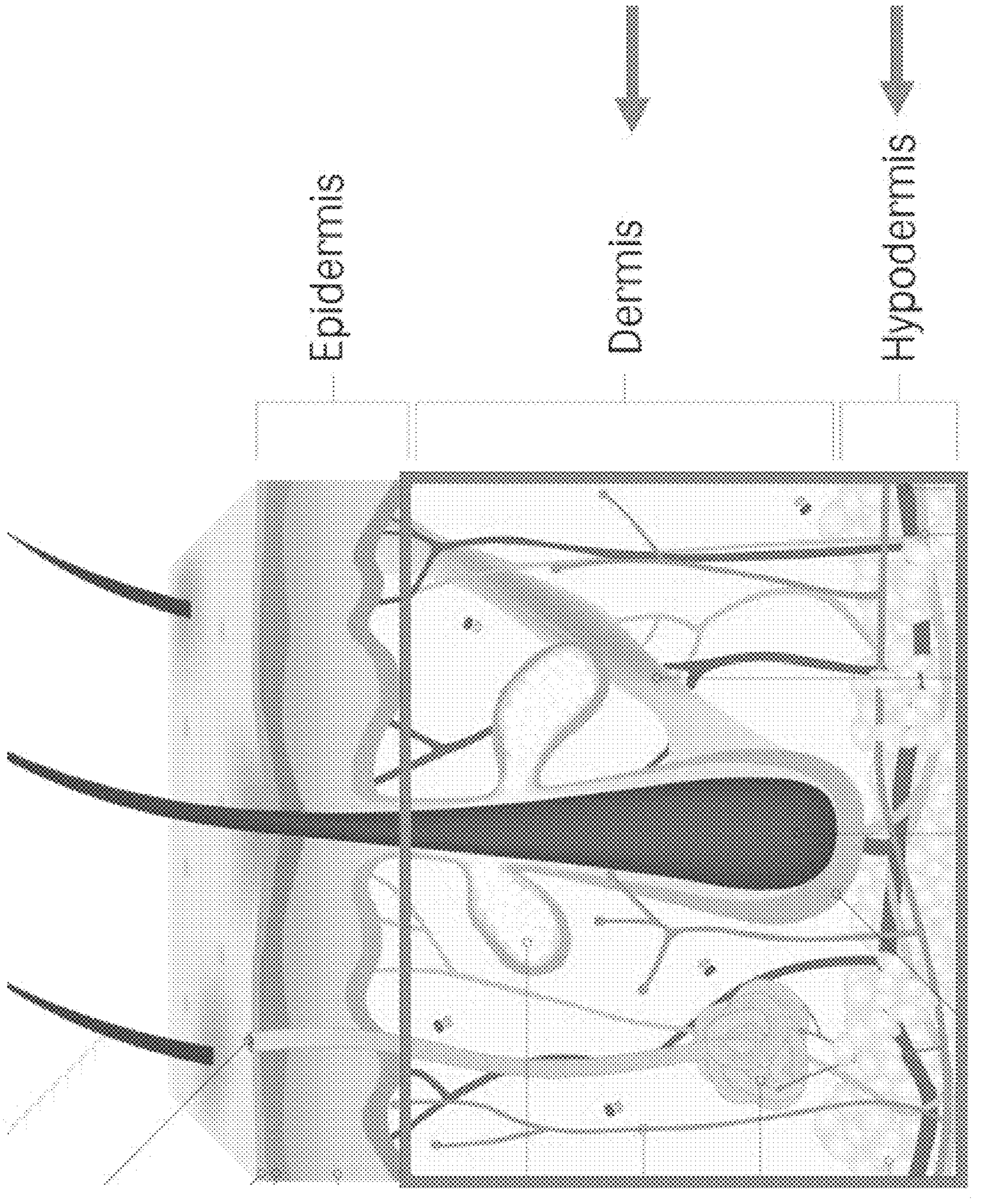
FIG. 1 illustrates a cross-section representation of human skin, showing the outer epidermis and interior dermis and hypodermis regions.

Repeat use of reference characters in the present specification and drawings is intended to represent the same or analogous features, elements, or steps of the presently disclosed subject matter.

DETAILED DESCRIPTION OF THE PRESENTLY DISCLOSED SUBJECT MATTER

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

In general, the present disclosure is directed to a system and methodology which relates to using infrared technology to detect tissue damage below the skin.

As is generally known, pressure injuries can occur whenever there is application of constant pressure, particularly if the pressure occurs at a bony area with minimal fat. Examples of such areas include the coccyx, shoulder blades, heels, and elbows. It is also known that damage can occur in a relatively short period of time, such as 2 hours.

Tissue damage can occur at a microvascular level, such as below the skin. FIG. 1 illustrates a cross-section representation of human skin, showing the outer epidermis and interior dermis and hypodermis regions.

Figures 2A, 2B, 2C, 2D, 2E, 3A, 3B, 3C, 3D, 3E:
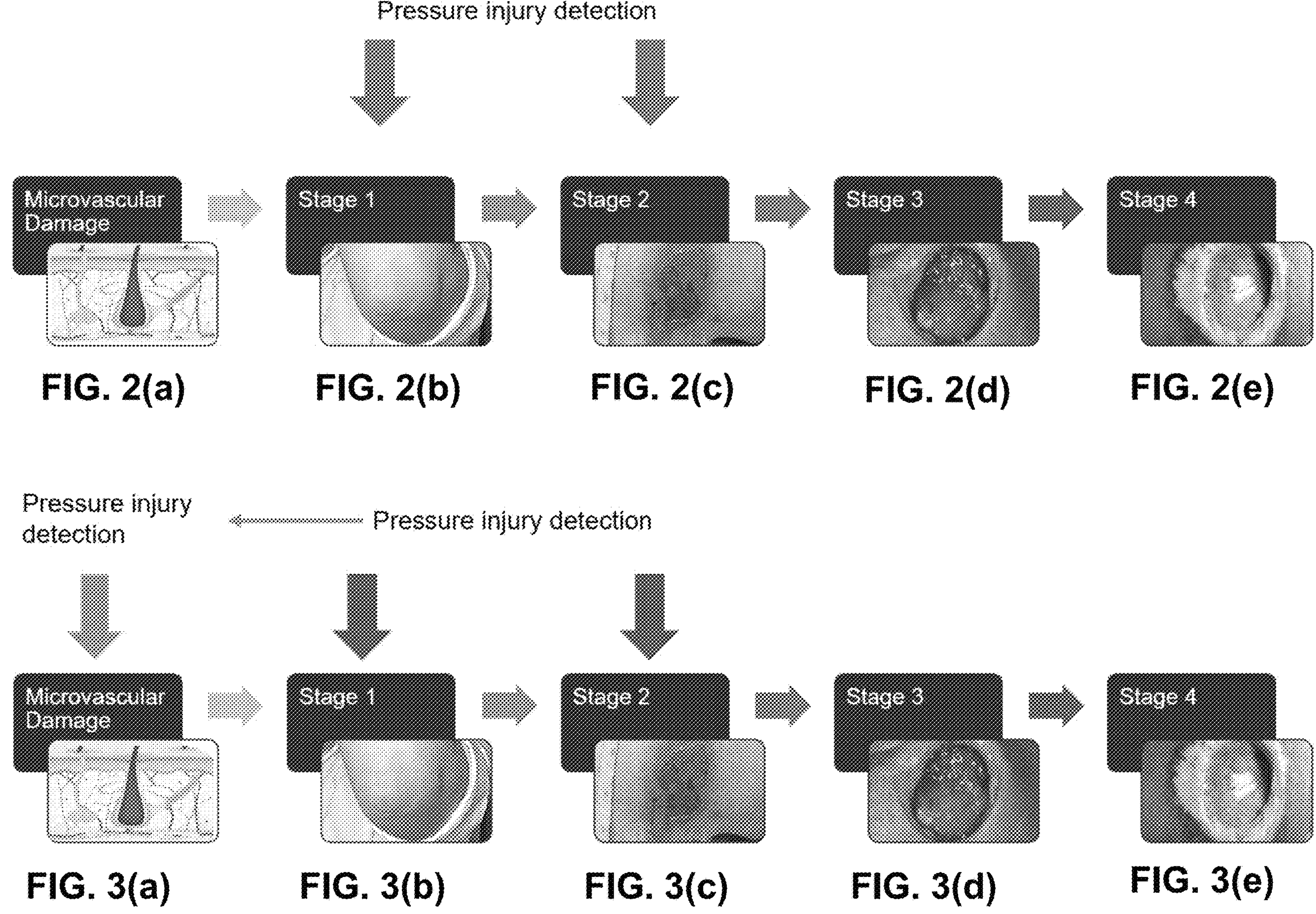
FIG. 2(*a*) illustrates a cross-section representation of microvascular damage.
FIGS. 3(*a*) through 3(*e*) respectively illustrate the same images of FIGS. 2(*a*) through 2(*e*) with respect to microvascular damage and respective Stage 1, Stage 2, Stage 3, and Stage 4 development of pressure ulcers, augmented by earlier indications of pressure injury detection.

FIG. 2(*a*) illustrates a cross-section representation of microvascular damage, while FIGS. 2(*b*) through 2(*e*) respectively illustrate a recognized progression of stages of microvascular damage (specifically, development of pressure ulcers) referred to as Stage 1, Stage 2, Stage 3, and Stage 4, respectively. Current practices typically result in pressure injury detection at either of Stage 1 or Stage 2, as represented particularly in conjunction with FIGS. 2(*b*) and 2(*c*). At Stage 1, per FIG. 2(*b*), the conditions are just erythema of the skin, meaning that ulcers have not yet broken through the skin. In Stage 2, as represented by FIG. 2(*c*), erythema is present with the loss of partial thickness of the skin including epidermis and part of the superficial dermis, meaning that ulcers have a break in the top two layers of skin. FIG. 2(*d*) represents an exemplary image of Stage 3, where a full thickness ulcer that might involve the subcutaneous fat, meaning that ulcers affect the top two layers of skin, as well as fatty tissue. FIG. 2(*e*) represents an exemplary Stage 4 image, where a full thickness ulcer includes involvement of the muscle or bone. In other words, Stage 4 pressure ulcers have developed to the point that deep wounds exist which may impact muscle, tendons, ligaments, and bone.

One significant goal of the presently disclosed subject matter is to intervene sooner than would otherwise occur, chiefly by early pressure injury detection (or prediction of existence). FIGS. 3(*a*) through 3 (*e*) respectively illustrate the same images of FIGS. 2(*a*) through 2(*e*) with respect to microvascular damage and respective Stage 1, Stage 2, Stage 3, and Stage 4 development of pressure ulcers, augmented by earlier indications of pressure injury detection. Thus, the figure-set of FIGS. 3(*a*)-3 (*e*) represents earlier pressure injury detection/prediction at Stage 1 or even before, per practice of the presently disclosed subject matter.

The presently disclosed subject matter provides a solution protocol particularly useful for example in acute care & long-term care facility settings. An example presently disclosed methodology may include in part, for example, the following ordered steps (or some subset thereof, such as Steps 1, 2, and 3):

1—Inspect Skin.
  - Such as using a Smartphone with infrared thermography.
  - For example, Nurse takes picture of skin (high-risk areas) (the specific frequency of such image capture can be varied per circumstances)

2—App
  - image data is uploaded into app.
  - the ambient temperatures of the area at the time of image capture is recorded, and the size and depth of any abnormalities are recorded 3—AI
  - per the uploaded image data, trained AI assesses images to detect changes over time
  - the appropriate medical personnel, such as a nurse, is alerted by the AI-based system of detected changes 4—Decision Support
  - The AI-based system provides decision support to medical personnel (such as nurse) in real-time based on an established protocol.
  - Link with Electronic Health Records (EHR) to initiate order-set (e.g., wound consult).

Existing technology makes use of thermal imaging to identify deep-tissue pressure injury on hospital admission of a patient. A known analyzer system ("WoundVision®") combines wound imaging and documentation, for the purpose of reducing clinical and financial burdens of hospital-acquired pressure injuries (by demonstrating the scope and level of prior/entry-time conditions).

An existing facet of using AI to prevent pressure ulcers in hospitals relates to determining patient positions which can lead to the development of pressure ulcers, to allow for patient repositioning as an attempted intervention. In particular, FIGS. 4(*a*) through 4(*c*) represent such existing technology. FIG. 4(*a*) is a simple image of a patient positioned on a support, as viewed from a position directly above the patient. FIG. 4(*b*) represents augmentation of the image by an associated AI-based system, to add lines representing the position of the patient's limbs and torso per the AI-based system analysis. FIG. 4(*c*) illustrates the added lines in isolation, coupled with a determination by the AI-based system that the patient is positioned on their left side. Accordingly, FIGS. 4(*b*) and 4(*c*) are marked as "Prior Art." Such AI-based system analysis allows the position/movement to be tracked for potential pressure ulcer development.

Various differences exist between the presently disclosed subject matter and the foregoing referenced existing technology. For example, the presently disclosed subject matter uses a Smartphone, infrared thermography, & an app to focus on early detection (of pressure ulcers) while the WoundVision® analyzer technology is a stand-alone device focusing on wound management rather than detection. Further, the presently disclosed subject matter uses AI to help identify condition changes over time and resulting decision support, while the WoundVision® analyzer technology does not include AI and does not include decision support.

The significance of the presently disclosed technology to addressing pressure ulcers or pressure injuries generally is borne out by the numbers, involving 2.5 million patients in the U.S. at a cost of $9.1-$11.6 billion, or average cost per patient of $43,000. If the cause of the pressure ulcer or injury occurs in a facility, there can be corresponding and/or associated financial responsibility. Treatments after the fact can range from surgery to dressings to expensive air mattress therapies, or mixes of all of the foregoing. Despite efforts, as many as upwards of 60,000 patients per year can die from associated conditions, resulting in potentially 17,000 lawsuits per year.

In addition to being effective relative to pressure ulcers or pressure injuries generally, the presently disclosed technology has additional healthcare applications, including but not limited to foot ulcers such as in patients with diabetes, necrotizing enterocolitis (NEC) in pre-term infants, and melanoma, among others.

As noted above, diabetic foot ulcers impact 15% of all diabetic patients in U.S., with corresponding significant risk of amputation. FIG. 5 illustrates an image of an example of a patient suffering with the impact of diabetic foot ulcers.

As known, necrotizing enterocolitis (NEC) in pre-term infants can impact upwards of 7-25% of all pre-term infants, reflecting 26,600-95,000 in U.S., with associates costs of $213 billion per year or costs of $500,000 per year per patient. Furthermore, NEC is the leading cause of death in NICU, impacting 7-30% of all pre-term infants, or on the order of about 26,600-114,000 deaths per year.

As noted above, the presently disclosed technology has additional healthcare applications in not only necrotizing enterocolitis (NEC) in pre-term infants, but also in conjunction with screening for melanoma, which otherwise already may have over 200,000 cases diagnosed each year in the U.S. Because a melanoma diagnosis may occur in Point-of-Care (POC) settings, it is often diagnosed in later stages, still with resulting costs upwards of $3.3 billion with as many as 8,000 deaths per year. In general, POC diagnosis have a higher mortality rate due to on-average later stage development when detected. FIGS. 6(*a*) and 6(*b*) illustrate respective images of examples of detected melanoma of a patient's skin.

Figures 7A, 7B, 7C, 7D, 7E, 8A, 8B, 8C, 8D, 8E:
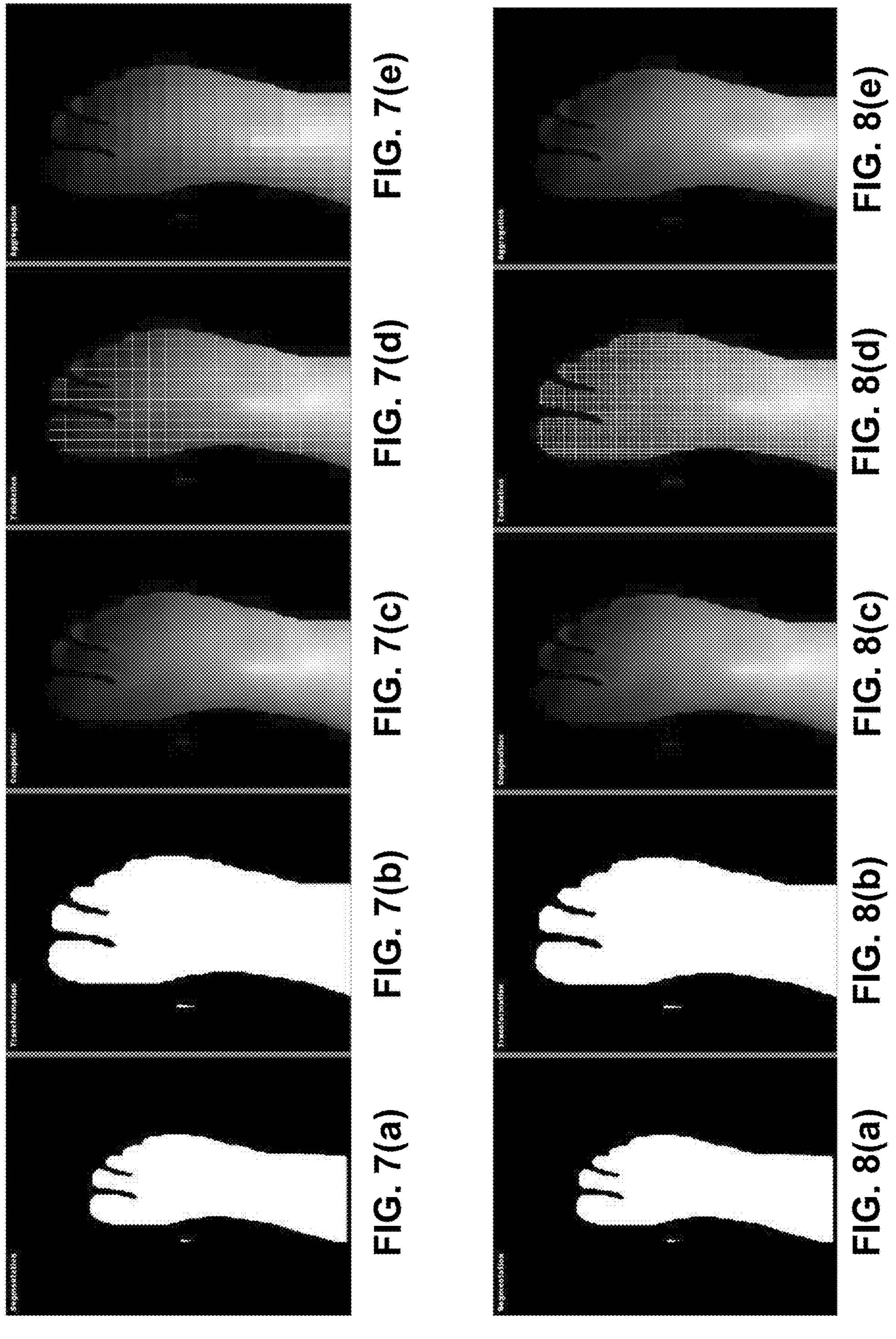
FIGS. 7(*a*) through 7(*e*) respectively illustrate presently disclosed image data processing steps of segmentation, transformation, composition, tabulation, and aggregation, for a given grid pattern.
FIGS. 8(*a*) through 8(*e*) respectively illustrate presently disclosed image data processing steps of segmentation, transformation, composition, tabulation, and aggregation, for another grid pattern different from that associated with FIGS. 7(*a*) through 7(*e*).

In yet further examples of presently disclosed technology, FIGS. 7(*a*) though 7(*e*) and FIGS. 8(*a*) through 8(*e*) represent steps through other aspects of present methodology specifically relating to processing of captured, uploaded image data. In particular, FIGS. 7(*a*) and 8(*a*) relate to a "segmentation" step while FIGS. 7(*b*) and 8(*b*) relate to "transformation." As will be understood from the complete disclosure herewith, the captured, uploaded image data created with a thermal scan is processed to remove the background to eliminate any potential external interference with the analysis. The process includes segmentation and transformation by generating a white image on a black background, as reflected by FIGS. 7(*a*) and 7(*b*), and 8(*a*) and 8(*b*).

As a next presently disclosed methodology step, the thermal image is integrated during a "composition" step, as represented by FIGS. 7(*c*) and 8(*c*).

Per a next presently disclosed methodology step referenced as "tabulation," a grid pattern is imposed on the thermal image of the foot (per the example presently represented in FIGS. 7(*a*) though 7(*e*) and FIGS. 8(*a*) through 8(*e*). For example, a grid pattern of 0.5"×0.25" or some other dimensional patterns (predetermined or otherwise contemporaneously selected) may be chosen for particular embodiments, as represented by the different patterns of FIGS. 7(*d*) and 8(*d*). The result of such operations is that the grid pattern creates cells organized in rows and columns, as represented by the subject figures.

As part of "aggregation" in the presently disclosed subject matter, the grid pattern for that embodiment is integrated into the thermal image. Furthermore, the temperature value in each cell is averaged.

Per presently disclosed subject matter, then a cell-by-cell comparison is performed. The comparison generates a second gride-like image that contains the temperature difference in each cell, as represented by each of FIGS. 7(*e*) and 8(*e*).

The processed captured image data as uploaded to the associated AI-based system/model, is then analyzed so that the AI-based system can perform anomaly detection and condition predictions. This used as part of the AI-based system evaluation to determine (or predict) whether an early detection is made of tissue damage below the skin (that is beneath the outer skin otherwise visible by the unaided eye of an observer).

Thus, FIGS. 7(*a*) through 7(*e*) respectively illustrate presently disclosed image data processing steps of segmentation, transformation, composition, tabulation, and aggregation, for a given grid pattern, while FIGS. 8(*a*) through 8(*e*) respectively illustrate presently disclosed image data processing steps of segmentation, transformation, composition, tabulation, and aggregation, for another grid pattern different from that associated with FIGS. 7(*a*) through 7(*e*).

This written description uses examples to disclose the presently disclosed subject matter, including the best mode, and also to enable any person skilled in the art to practice the presently disclosed subject matter, including making and using any devices or systems and performing any incorporated methods. The patentable scope of the presently disclosed subject matter is defined by the claims, and may include other examples that occur to those skilled in the art. Such other examples are intended to be within the scope of the claims if they include structural and/or step elements that do not differ from the literal language of the claims, or if they include equivalent structural and/or elements with insubstantial differences from the literal languages of the claims. In any event, while certain embodiments of the disclosed subject matter have been described using specific terms, such description is for illustrative purposes only, and it is to be understood that changes and variations may be made without departing from the spirit or scope of the subject matter. Also, for purposes of the present disclosure, the terms "a" or "an" entity or object refers to one or more of such entity or object. Accordingly, the terms "a", "an", "one or more," and "at least one" can be used interchangeably herein.

What is claimed is:

1. Methodology for detecting tissue damage below a patient's skin, comprising:

capturing a plurality of time-spaced infrared thermography images for selected regions of the patient's skin;

recording ambient temperatures at the selected regions at each time that the plurality of time-spaced infrared thermography images are captured; and processing the captured time-spaced infrared thermography images image data to create resulting data;

wherein processing the captured time-spaced infrared thermography images includes removing background in the image created with the infrared thermography image data to eliminate any potential external interference with the analysis, to generate a white image on a black background;

integrating a thermal image into the white image;

imposing a grid pattern on the integrated thermal and white image and creating cells organized in rows and columns; and averaging a temperature value in each cell on the integrated thermal and white image; and the methodology further includes uploading the processed captured time-spaced infrared thermography images and the recorded ambient temperatures into a trained machine-learning model, wherein the trained machine-learning model is trained to perform analysis to identify deviations in skin temperature of the patient and detect tissue damage below the patient's skin based on identified skin temperature deviations.

2. Methodology according to claim 1, wherein the patient is a Diabetes Mellitus patient, and the machine-learning model is trained to identify to detect changes in temperature related to blood flow alterations, and detect an emerging DFU (Diabetic Foot Ulcer) in the DM (Diabetes Mellitus) patient through the identified deviations in skin temperature.

3. Methodology according to claim 1, wherein capturing the plurality of time-spaced infrared thermography images comprises a user using a smartphone equipped with infrared thermography to take pictures of selected regions of skin, at a predetermined frequency between image captures.

4. Methodology according to claim 3, wherein the selected regions of skin comprise bony areas with minimal fat included but not limited to one of the patient's coccyx, shoulder blades, heels, and elbows.

5. Methodology according to claim 1, wherein the trained machine-learning model is trained to:

assess the captured time-spaced infrared thermography images to detect changes over time, and provide decision support in real-time to authorized medical personnel regarding patient course of treatment.

6. Methodology according to claim 5, wherein providing decision support further includes making automatic entries in Electronic Health Records (EHR) for retrieval by the authorized medical personnel regarding patient course of treatment including informed intervention actions.

7. Methodology according to claim 1, wherein the trained machine-learning model comprises a convolution neural network with multiple convolutional layers.

8. Methodology according to claim 1, wherein processing the captured time-spaced infrared thermography images includes providing:

one or more processors; and one or more non-transitory computer-readable media that store instructions that, when executed by the one or more processors, cause the one or more processors to perform operations of the processing.

9. Methodology according to claim 8, wherein the trained machine-learning model is further trained to:

perform a cell-by-cell comparison to generate a second grid-like image that contains the temperature deviations in each cell; and perform anomaly detection and condition predictions.

10. Methodology according to claim 1, wherein processing the captured time-spaced infrared thermography images further includes conducting image processing steps of segmentation, transformation, composition, tabulation, and aggregation, per the grid pattern imposed on the time-spaced infrared thermography images.

11. Methodology according to claim 1, wherein the trained machine-learning model is further trained to detect and identify at least one of tissue damage in diabetic patients, melanoma, necrotic colitis in pre-term infants, and any other condition where a temperature change occurs due to an inflammatory response or other type of response.

12. Methodology for using infrared technology for detecting tissue damage below a patient's skin, comprising:

using a smartphone equipped with infrared thermography to capture a plurality of time-spaced infrared thermography images of selected regions of the patient's skin, at predetermined frequency between image captures;

recording the ambient temperatures at the selected regions at each time that the plurality of time-spaced infrared thermography images are captured; and processing the captured time-spaced infrared thermography images to create resulting data;

wherein processing the captured time-spaced infrared thermography images includes removing background in the captured time-spaced infrared thermography images to eliminate any potential external interference with the analysis, to generate a white image on a black background;

integrating a thermal image into the white image;

imposing a predetermined grid pattern on the integrated thermal and white image and creating cells organized in rows and columns;

averaging a temperature value in each cell on the integrated thermal and white image; and the methodology further includes uploading the processed captured time-spaced infrared thermography images and recorded ambient temperatures into a trained machine-learning model, wherein the machine-learning model is trained to assess the processed time-spaced infrared thermography images to detect changes over time to identify deviations in skin temperature of the patient, to detect tissue damage below the patient's skin based on identified skin temperature deviations, and to provide decision support in real-time to medical personnel regarding patient course of treatment, wherein the machine-learning model is trained to perform analysis to detect and identify at least one of tissue damage in diabetic patients, melanoma, necrotic colitis in pre-term infants, and any other condition where a temperature change occurs due to an inflammatory response or other type of response.

13. Methodology according to claim 12, wherein the selected regions of skin comprise bony areas with minimal fat included but not limited to one of a patient's coccyx, shoulder blades, heels, and elbows.

14. Methodology according to claim 12, wherein the machine-learning model comprises a convolution neural network with multiple convolutional layers.

15. Methodology according to claim 12, wherein the trained machine-learning model is further trained to:

perform a cell-by-cell comparison to generate a second grid-like image that contains the temperature deviations in each cell; and perform anomaly detection and condition predictions.

16. Methodology according to claim 12, wherein providing decision support further includes making automatic entries in Electronic Health Records (EHR) for retrieval by the medical personnel regarding patient course of treatment including informed intervention actions.

17. Methodology according to claim 12, wherein processing the captured time-spaced infrared thermography images includes providing:

one or more processors; and one or more non-transitory computer-readable media that store instructions that, when executed by the one or more processors, cause the one or more processors to perform operations of the processing.

* * * * *